(12) United States Patent
Luke et al.

(10) Patent No.: US 7,927,482 B1
(45) Date of Patent: Apr. 19, 2011

(54) METHOD AND SYSTEM FOR CONTAINING AND REMOVING DENTAL WASTE

(75) Inventors: Stephen A Luke, Coopersville, MI (US); Grayle D Woodruff, Nunica, MI (US)

(73) Assignee: G & S Mercury Recovery Systems, LLC, Coopersville, MI (US)

( * ) Notice: Subject to any disclaimer, the term of this patent is extended or adjusted under 35 U.S.C. 154(b) by 507 days.

(21) Appl. No.: 11/401,583

(22) Filed: Apr. 11, 2006

Related U.S. Application Data

(60) Provisional application No. 60/670,411, filed on Apr. 12, 2005.

(51) Int. Cl.
*B01D 21/30* (2006.01)
*B01D 29/00* (2006.01)
*C02F 9/00* (2006.01)
*E03B 5/00* (2006.01)
*E03B 11/00* (2006.01)
*B01D 19/00* (2006.01)

(52) U.S. Cl. ...... 210/136; 210/137; 210/241; 210/257.1; 210/258; 137/565.01; 137/571; 96/193

(58) Field of Classification Search ............... 433/92, 433/97; 210/136, 137, 188, 241, 257.1, 258, 210/259; 137/565.01, 571; 96/155, 193
See application file for complete search history.

(56) References Cited

U.S. PATENT DOCUMENTS

| 4,245,989 | A | * | 1/1981 | Folkenroth et al. | 433/92 |
| 5,795,159 | A | | 8/1998 | Ralls et al. | |
| 5,879,552 | A | * | 3/1999 | Bradfield | 210/411 |
| 5,885,076 | A | | 3/1999 | Ralls et al. | |
| 6,592,754 | B2 | | 7/2003 | Chilibeck | |
| 6,692,636 | B2 | * | 2/2004 | Chilibeck | 210/137 |
| 2002/0174778 | A1 | * | 11/2002 | Petrusha | 99/336 |
| 2003/0003417 | A1 | * | 1/2003 | Hubner et al. | 433/92 |

OTHER PUBLICATIONS

Stone, et al. The Management of Mercury in the Dental-Unit Wastewater Stream, Scientific Review of Issues Impacting Dentistry, Jan. 2000, vol. 2, No. 1.

* cited by examiner

*Primary Examiner* — Cris L Rodriguez
*Assistant Examiner* — Matthew M Nelson
(74) *Attorney, Agent, or Firm* — Van Dyke, Gardner, Linn & Burkhart, LLP (57) ABSTRACT

A dental waste containment and removal system and method for containing and removing dental waste produced at a dental services facility involves transferring dental waste containing a contaminant such as mercury from a patient's mouth into a dental waste container under a vacuum pressure such that the dental waste is temporarily retained within the dental waste container. The dental waste may then be removed from the dental waste container from a remote location, such as from the exterior of the dental facility, by pumping or suctioning the dental waste, and transported to a treatment facility.

14 Claims, 7 Drawing Sheets

METHOD AND SYSTEM FOR CONTAINING AND REMOVING DENTAL WASTE

CROSS REFERENCE TO RELATED APPLICATION

The present application claims priority of U.S. provisional application Ser. No. 60/670,411, filed Apr. 12, 2005, by Stephen A. Luke and Grayle D. Woodruff for METHOD AND SYSTEM FOR CONTAINING AND REMOVING DENTAL WASTE, which is hereby incorporated herein by reference in its entirety.

BACKGROUND AND TECHNICAL FIELD OF THE INVENTION

The present invention is embodied in a system and method for containing and removing contaminated dental waste from a dental services facility. In particular, a preferred embodiment of the invention enables the capture of mercury contaminated dental waste.

Mercury is a highly toxic, persistent, and bio-accumulative pollutant. Once released, mercury can remain in the environment for years with the potential to disperse over a wide area posing a significant risk to human health, wildlife and the environment. Health effects of mercury are particularly severe to fetuses and younger children.

Dental service facilities are among the largest users of mercury in the United States. Dental practices use mercury in the filling of cavities and repairing of fillings in procedures referred to as amalgam restorations. Amalgam is used to fill cavities in teeth and is composed of powdered mercury, silver, and tin, and may contain other elements. During procedures with or on fillings, the powdered mercury gets into the dental waste lines of the dental facility by being suctioned or rinsed out of a patient's mouth with a saliva ejector that is used in connection with dental evacuation devices, the mercury being in a state of suspension in the water/saliva mixture.

Typically, such dental waste produced at dental service facilities is released into the sewer lines that deliver waste water to waste water treatment facilities. The average dentist office produces over two pounds of waste a year, with the mercury produced by dental practices contributing to the significant mercury levels in municipal wastewater treatment plants, which are not designed to treat or reduce mercury contaminated waste water.

Accordingly, there is a need for a safe, effective, and cost efficient method of preventing dental waste containing mercury that is produced at a dental services facility from being released into the environment.

SUMMARY OF THE INVENTION

The present invention provides a system and method for containing and removing dental waste contaminated with mercury, or the like, from a dental services facility by capturing the contaminated dental waste for later transportation to a treatment facility for processing.

According to one aspect of the present invention, a method of containing and removing contaminated dental waste generated at a dental services facility comprises generating a vacuum pressure within a first dental waste container that is generally fixedly installed within a dental services facility and adapted to receive contaminated dental waste. The method includes suctioning dental waste containing a contaminant from the mouth of a dental patient via the vacuum pressure generated within the first dental waste container, transferring the dental waste suctioned from the patient's mouth to the first dental waste container, and retaining the dental waste temporarily in the first dental waste container. The method also includes removing the dental waste from the first dental waste container, transporting the dental waste to a treatment facility, and processing the dental waste.

According to another aspect of the present invention, a dental waste system for containing and removing contaminated dental waste produced at a dental facility comprises at least a first dental waste container generally fixedly installed within a dental waste facility and adapted to receive contaminated dental waste. A vacuum conduit is connected to the first dental waste container and a vacuum pump connected to the vacuum conduit is adapted to selectively generate a vacuum pressure within the first dental waste container. A suction conduit in fluid communication with the first dental waste container is operable in response to the vacuum pressure generated by the vacuum pump to transfer dental waste containing a contaminant from the mouth of a dental patient to the first dental waste container. A waste removal conduit in fluid communication with the first dental waste container and is adapted to enable removal of dental waste from the first dental waste container.

The dental waste containment system and method of the present invention provides an effectively prevents contaminated dental waste from entering a sewer line and/or ground water. The dental waste captured in the dental waste container may be easily pumped out of the dental waste container from a remote location, such as through an exterior wall of the dental facility to a transport tank on a service vehicle. The dental waste may then be readily delivered to a treatment facility that is able to effectively remove or treat contaminants such as mercury. The providing of indicators or gauges on the dental waste containers provides an effective method of notifying the dental services facility personnel, or a dental waste service provider, that the dental waste container has been filled with a predetermined level of dental waste and needs to be emptied or replaced. Further, a dental waste containment system constructed to include two dental waste containers, one of which functions as an accumulator tank and the other as a storage tank, provides an effective construction for collecting, for example, daily waste and retaining longer term waste.

These and other objects and advantages will become more apparent from a study of the drawings and description that follow.

DESCRIPTION OF THE PREFERRED EMBODIMENTS

The present invention will now be described with reference to the accompanying drawings, wherein the reference numerals in the following written description correspond to like-numbered elements in the several drawings.

Figure 1:
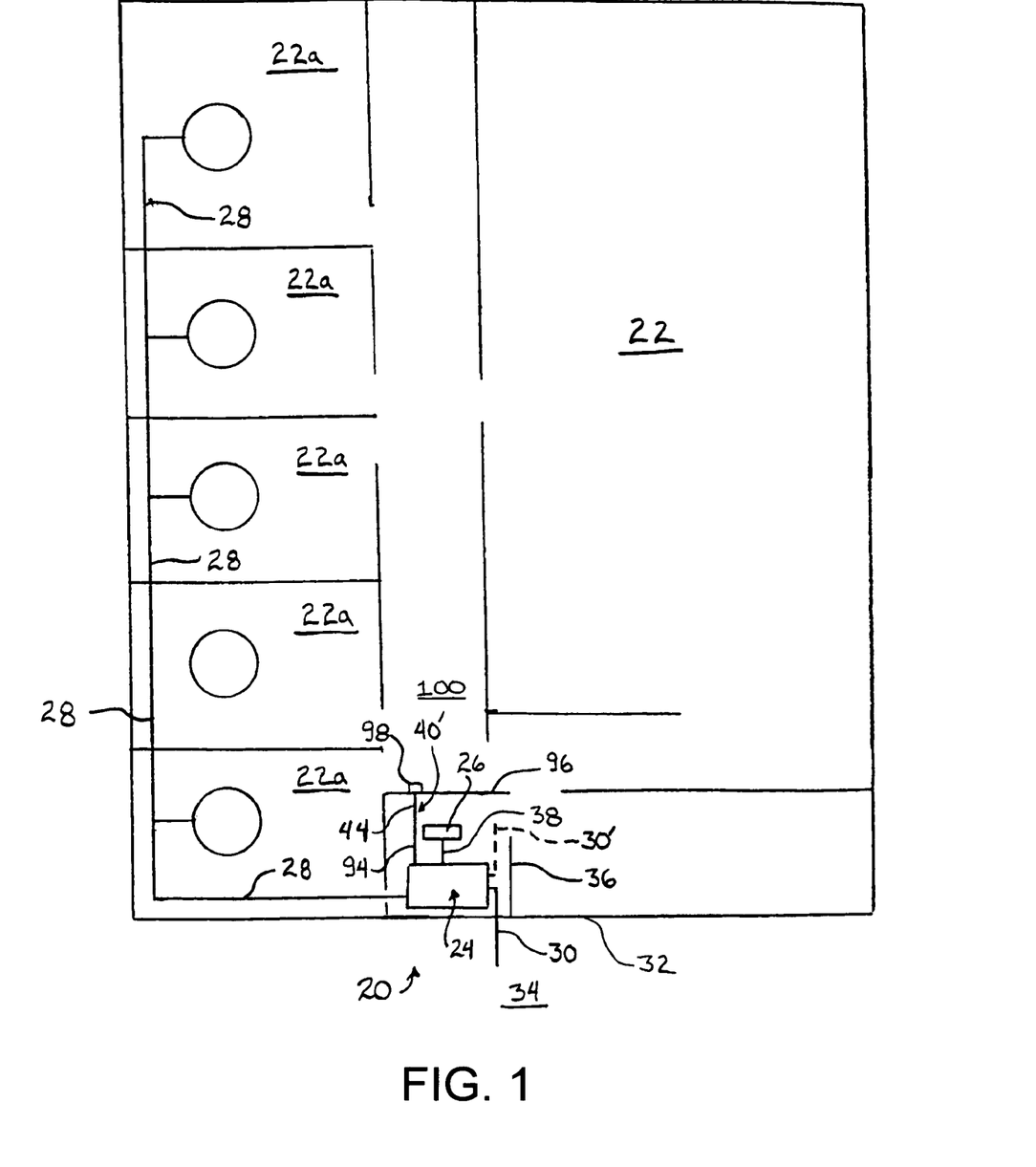
FIG. 1 is a schematic plan view of a dental service facility employing the system and method of the present invention.

A dental waste system or dental waste containment system, shown generally at 20 in FIG. 1, is used to capture dental waste produced at a dental facility 22. Dental waste system 20 includes a dental waste container 24 that is generally fixedly installed within the facility 22 and which is connected to a suction device or dental evacuation device, such as a suction pump or vacuum pump 26 (FIGS. 2 and 3), to create or generate a vacuum pressure within dental waste container 24. A suction line 28 extending from dental waste container 24 to each of the rooms 22a of the dental facility 22 enables a dentist, oral hygienist, orthodontist, or the like, to transfer dental waste 71 (FIG. 2) containing a contaminant, such as amalgam, and/or saliva and/or blood, or the like, from a patient's mouth to dental waste container 24 via the generated vacuum pressure. For example, a dental hygienist may evacuate a patient's mouth using a conventional saliva ejector that is connected to suction line 28 or by directing a patient to spit into a conventional dental sink or bowl connected to suction line 28.

The contaminated dental waste 71 transferred to the dental waste container 24 is then later removed, such as by pumping out the dental waste 71, from the dental waste container 24 for proper processing to substantially remove or render harmless the contaminants that are contained in the dental waste 71. In the illustrated embodiment of FIG. 1, dental waste system 20 includes a waste removal or discharge line or conduit 30 which extends through exterior wall 32 of dental facility 22 to an exterior location 34 to enable the dental waste 71 to be pumped out of dental waste container 24 without bringing additional equipment into the dental facility 22. Dental waste system 20, therefore, substantially prevents dental waste 71 containing a contaminant, such as suspended mercury, from entering a sewer line (not shown) or from entering the ground water.

Figure 2:
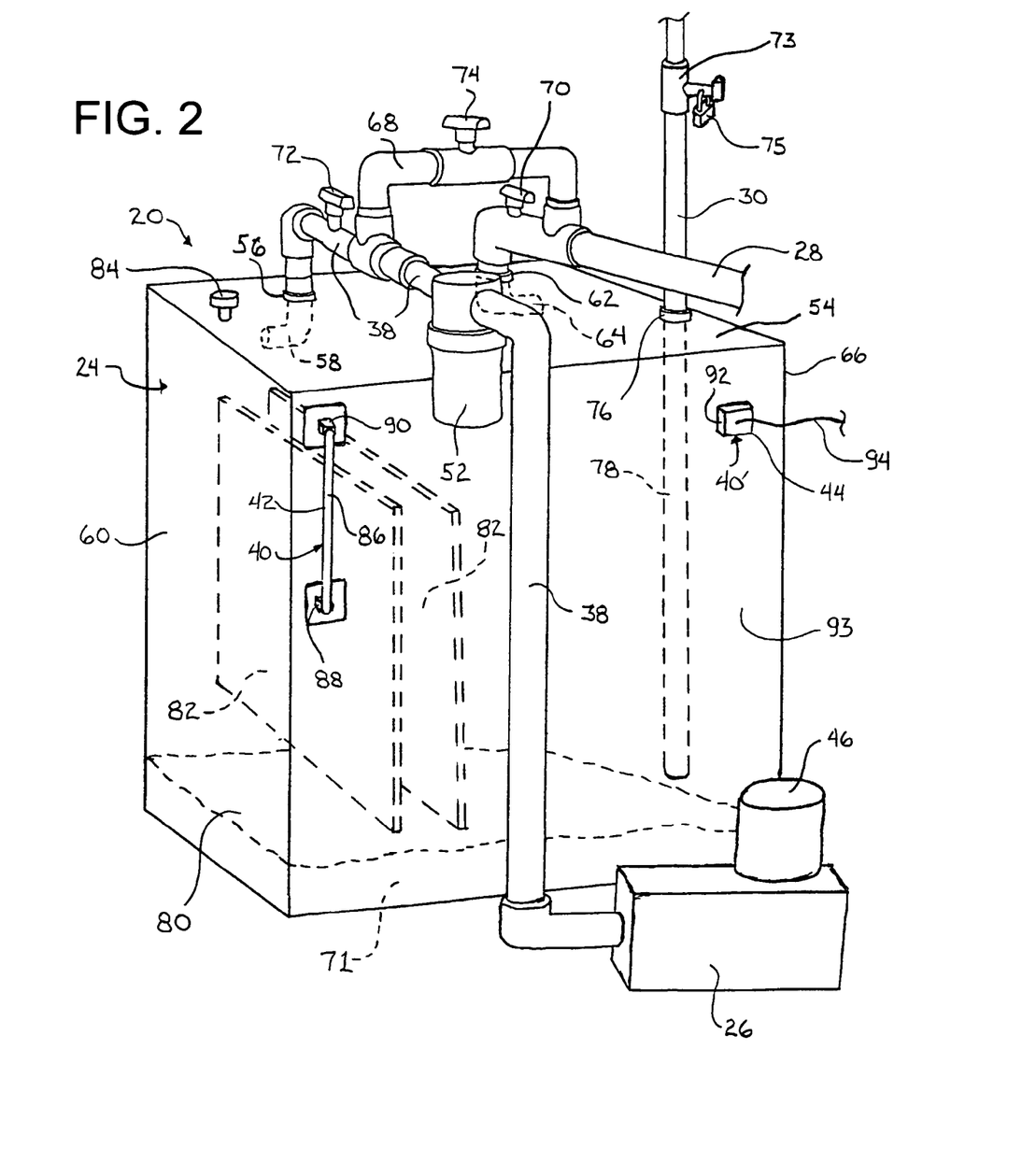
FIG. 2 is a perspective view of a dental waste containment system of the present invention.
Figure 3:
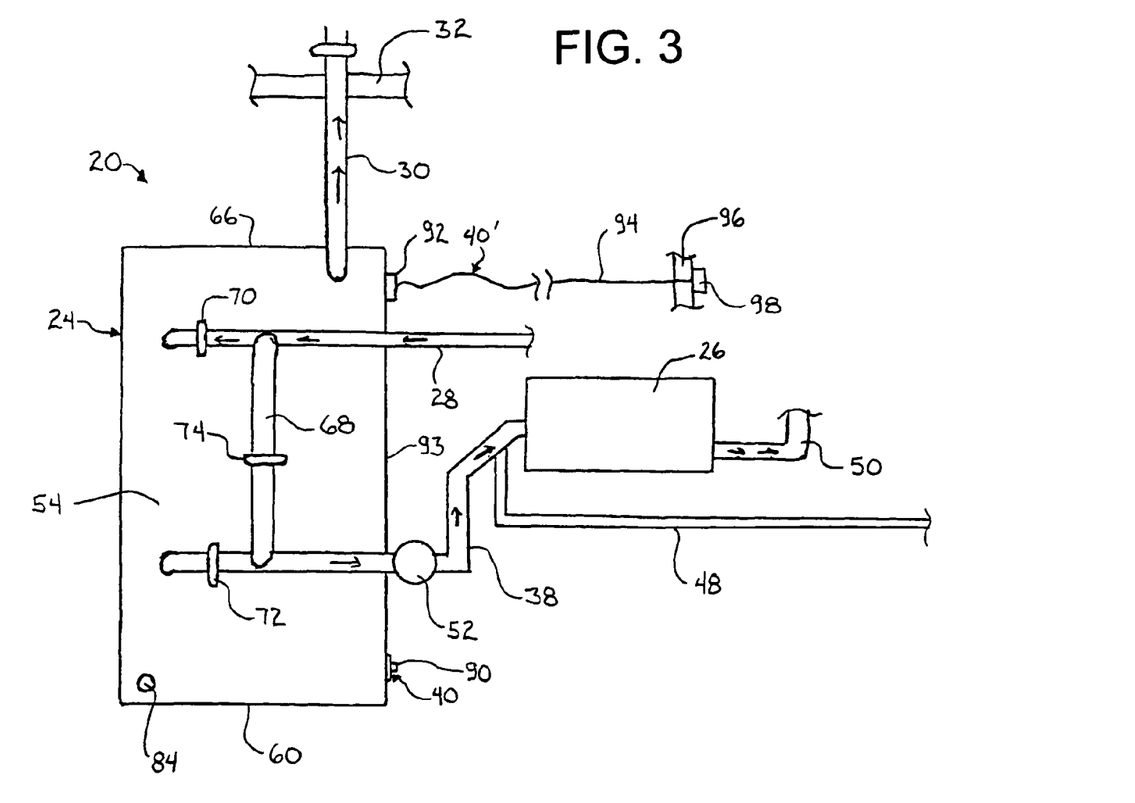
FIG. 3 is a top plan view of the dental waste containment system of FIG. 2.

Referring now to FIGS. 2 and 3, dental waste containment system 20 is generally fixedly mounted or installed and substantially located within a facilities room 36 of the dental facility 22, which may be in a basement of the dental facility 22. In the illustrated embodiment, dental waste containment system 20 includes a dental waste container 24 and a vacuum pump 26 connected to dental waste container 24 by a vacuum line or conduit 38. Dental waste containment system 20 also includes, as noted above, a suction line or conduit 28, and a waste removal line or conduit 30. Dental waste container 24 may further include indicators 40, 40' for detecting the level of dental waste within dental waste container 24, such as a visual gauge 42, and an electronic or electrical gauge 44, which may be constructed as a light indicating gauge, and/or an audible indicating gauge, as described below.

In the illustrated embodiment, dental waste container 24 is constructed to have a generally cubic form and is constructed of a metallic material, such as aluminum or stainless steel, or may include a coating. Dental waste containers may be constructed to have volumetric capacities corresponding to the amount of dental waste produced by a particular dental facility. For example, the dental waste container may be sized to contain the dental waste produced in one or more days, weeks, or months from a dental facility. Alternatively, a dental waste container may be constructed of a polymeric material and still function as intended within the scope of the present invention.

As previously noted, vacuum or suction pump 26, via electric motor 46, creates a vacuum pressure within dental waste container 24 by pulling or drawing substantially only air or gas from dental waste container 24 through vacuum conduit 38 such that dental waste 71 is deposited and retained within dental waste container 24. Vacuum pump 26 may be constructed as either a wet system or a dry system, wherein a wet system may draw both air and liquid while a dry system is constructed to draw only air. In the case of a wet system, the liquid drawn may be used to cool and/or lubricate the pump. In the illustrated dental waste system 20, however, liquefied dental waste 71 is desirably retained within dental waste container. Therefore, as illustrated in FIG. 3, a separate water line 48, such as a conventional water line of the dental facility supplied by either a well or city utility, may be connected to the vacuum conduit 38. Because vacuum conduit 38 only draws air and/or gas and does not draw dental waste 71, the dental waste 71 does not mix with water supplied by line 48 such that a water discharge conduit 50 may, for example, be directed to a sewer line (not shown) without contaminating the water supply.

A filter 52 is connected to vacuum conduit 38 for removing odors or purifying air drawn from dental waste container 24. Filter 52 may be a HEPA filter, charcoal filter, or the like. Vacuum conduit 38 is attached to the top 54 of dental waste container 24 at a vacuum connection 56 and a vacuum tube 58 may extend internally into dental waste container 24. Vacuum tube 58, in the illustrated embodiment, is directed toward side 60 of dental waste container 24 to inhibit or impede the drawing of dental waste 71 directly into vacuum conduit 38 from suction conduit 28, as described in more detail below. In the illustrated embodiment, vacuum conduit 38 and vacuum tube 58 are constructed as separate components; however, vacuum conduit 38 and vacuum tube 58 may alternatively be constructed, for example, as a unitary pipe with vacuum connection forming a seal between such a unitary pipe and the dental waste container.

Suction conduit 28 is attached to the top 54 of dental waste container 24 at suction connection 62 and a suction tube 64 may extend internally into dental waste container 24. Suction connection 62, in the illustrated embodiment, is positioned approximately 18 to 20 inches, for example, from vacuum connection 56 to inhibit or impede the drawing of dental waste 71 directly into vacuum conduit 38 from suction conduit 28. Suction tube 64 is directed toward side 66 of dental waste container 24, which is opposite to the side 60 at which vacuum tube 58 is directed, to further inhibit or impede the drawing of dental waste 71 directly into vacuum conduit 38 from suction conduit 28. In the illustrated embodiment, suction conduit 28 and suction tube 64 are constructed as separate components, however, suction conduit and suction tube may alternatively be constructed, for example, as a unitary pipe with suction connection forming a seal between such a unitary pipe and the dental waste container.

FIGS. 2 and 3 also illustrate the inclusion of a bypass conduit or line 68 connecting suction conduit 28 and vacuum conduit 38, and the inclusion of a suction line valve 70, vacuum line valve 72, and bypass line valve 74. When suction line valve 70 and vacuum line valve 72 are open and bypass line valve 74 is closed, dental waste 71 drawn through suction line 28 is deposited into dental waste container 24. However, when suction line valve 70 and vacuum line valve 72 are closed and bypass line 74 valve is open, dental waste drawn through suction line 28 is transferred directly to vacuum line 38 and drawn towards vacuum pump 26. This situation may be employed in the event dental waste container 24 is full or requires repair or maintenance. In such a situation, for example, dental waste may be transferred to a secondary dental waste container or drum or tank (not shown). Alternatively, the dental waste may be directed to a sewer line, such as, for example, during procedures wherein a contaminant may not be contained within the dental waste.

In the illustrated embodiment, vacuum conduit 38, suction conduit 28, and bypass conduit 68 are constructed of 1½ inch diameter PVC tubing. It should be appreciated, however, that alternative sizes, materials, and positioning and/or directing of vacuum conduit, vacuum connection, vacuum tube, suction conduit, suction connection, and suction tube may be employed within the scope of the present invention. For example, a vacuum and/or suction connection may be located on a side of dental waste container. Further, the vacuum and suction connections may be positioned apart from each other either a greater or lesser distance. Vacuum conduit, suction conduit, and/or bypass conduit may also be alternatively constructed of copper or galvanized steel tubing, and/or may be constructed to have greater or smaller diameters.

Waste removal conduit or line or discharge conduit or line 30, as noted above, is attached to dental waste container 24 at removal line connection 76 and a waste removal tube 78 extends internally into dental waste container 24 toward a bottom portion 80 of the dental waste 71 container 24. Waste removal conduit 30 is used to transfer dental waste out of dental waste container 24, such as by pumping or suctioning out, to a vessel used to transport the waste for treatment at a processing facility, described in more detail below. As shown in FIG. 1, waste removal conduit 30 may extend through or out of an external wall 32 of the dental facility 22 such that the dental waste 71 may be readily removed from the dental waste container 24 and dental facility 22, as described in more detail below. Alternatively and/or additionally, however, as also indicated in FIG. 1, a waste removal conduit 30' may extend or be located within the dental facility 22 whereby a transport vessel or a hose extending from a transport vessel is brought into the dental facility 22 to suction or pump the dental waste 71 from dental waste container 24.

As shown in FIG. 2, a valve 73 having a locking mechanism 75 may be placed on waste removal conduit to prevent unauthorized removal of dental waste 71 from dental waste container 24. Although valve 73 and locking mechanism 75 are shown located within an interior location proximate dental waste container 24, it should be appreciated that a valve and lock may alternatively or additionally be located on the waste removal conduit 30 at an exterior location 34 of the dental facility 22.

In the illustrated embodiment, waste removal conduit 30 and waste removal tube 78 are separate components, with conduit 30 formed of one inch diameter PVC tubing. However, waste removal conduit 30 and waste removal tube 78 may alternatively be constructed as a unitary member and/or may be made from copper or galvanized tubing, or the like.

Dental waste container 24 may also include internal baffles or supports 82 and a vacuum pressure regulator 84 to control the vacuum pressure within dental waste container 24. In the illustrated embodiment, baffles 82 are constructed as metallic plates fixed to the interior of dental waste container 24, such as by welding. Baffles 82 may be used to inhibit or impede the intake of dental waste 71 into vacuum line 38, the dental waste 71 having a liquefied nature and delivered or suctioned into dental waste container 24 at high velocity. In addition, baffles 82 may function to provide support to dental waste container 24 to prevent deformation or collapsing of the container 24.

FIG. 2 discloses the inclusion of an indicator 40 formed as a visual gauge 42 for monitoring the level of dental waste 71 contained within dental waste container 24. Visual gauge 42 includes a sight tube 86 formed as a transparent or translucent tube. Dental waste 71 is able to flow into sight tube 86 through lower fitting 88, up sight tube 86, and back into dental waste container 24 through upper fitting 90. Although shown as including a single visual gauge 42 extending a portion of the height of dental waste container 24, it should be appreciated that additional visual gauges may be included on dental waste container 24, such as in an offset vertical relationship, to monitor dental waste levels. Alternatively, a single visual gauge may be employed that extends a greater amount of the vertical height of dental waste container 24.

FIGS. 2 and 3 disclose an indicator 40' constructed as an electronic gauge 44 for detecting dental waste 71 fluid levels that may be included on dental waste system 20 in addition to visual indicator 40, or alternatively, may be included on dental waste system 20 instead of visual indicator 40. As described below, electronic gauge 44 may be formed as a light indicating gauge and/or an audible indicating gauge. In the illustrated embodiment, electronic gauge 44 includes a base 92 mounted to dental waste container 24 having a fluid sensor (not shown) that may be disposed internally of dental waste container 24, or may be adapted to detect dental waste 71 entering base 92 through sidewall 93 of dental waste container 24, or operate in a similar known manner. Base 92 transmits a signal through line 94, which may pass through a wall 96 of dental facility 24 (FIGS. 1 and 3) to a receiver member 98. Alternatively, base 92 may wirelessly transmit a signal to receiver member 98, such as by a radio frequency, cellular phone signal, or the like. Further, such a wireless transmission may be additionally or alternatively transmitted directly to a dental waste service provider remote from the dental facility.

In the illustrated embodiment of FIGS. 1 and 3, receiver member 98 is disposed within an internal location 100 of dental facility 22. Receiver member 98 is adapted to provide a sensory signal to occupants or employees of the dental facility 22 to alert them to the level of dental waste 71 within dental waste container 24, thus, receiver 98 may be constructed to provide either an audible signal, such as an alarm buzzer, and/or a visual signal, such as a flashing light, for example. Thus, electronic gauge 44 may be formed as a light indicating gauge when receiver 98 emits a light signal, and/or may be formed as an audible indicating gauge when receiver 98 emits an audible sound.

In response to a determination of a predetermined dental waste 71 fluid level, such as by visually observing visual gauge 42 and/or sensing a signal from electronic gauge 44, a dental facility employee may contact a removal service to pump out or evacuate dental waste container 24. Alternatively, a dental waste facility employee may be trained to transfer the dental waste 71 into individual containers, canisters, tanks, or the like, for later pickup by a removal service. Still further, in the embodiment of a wireless transmission by an electronic gauge 44 to a dental waste service provider, a service truck may be dispatched automatically to the dental facility 22 to remove the dental waste 71.

Although dental waste container 24 is shown as including both a visual gauge 42 and an electronic gauge 44, it should be understood that dental waste container 24 may alternatively be constructed to include only one of such gauge types, or the dental waste container 24 may be constructed without such gauges.

Figure 4:
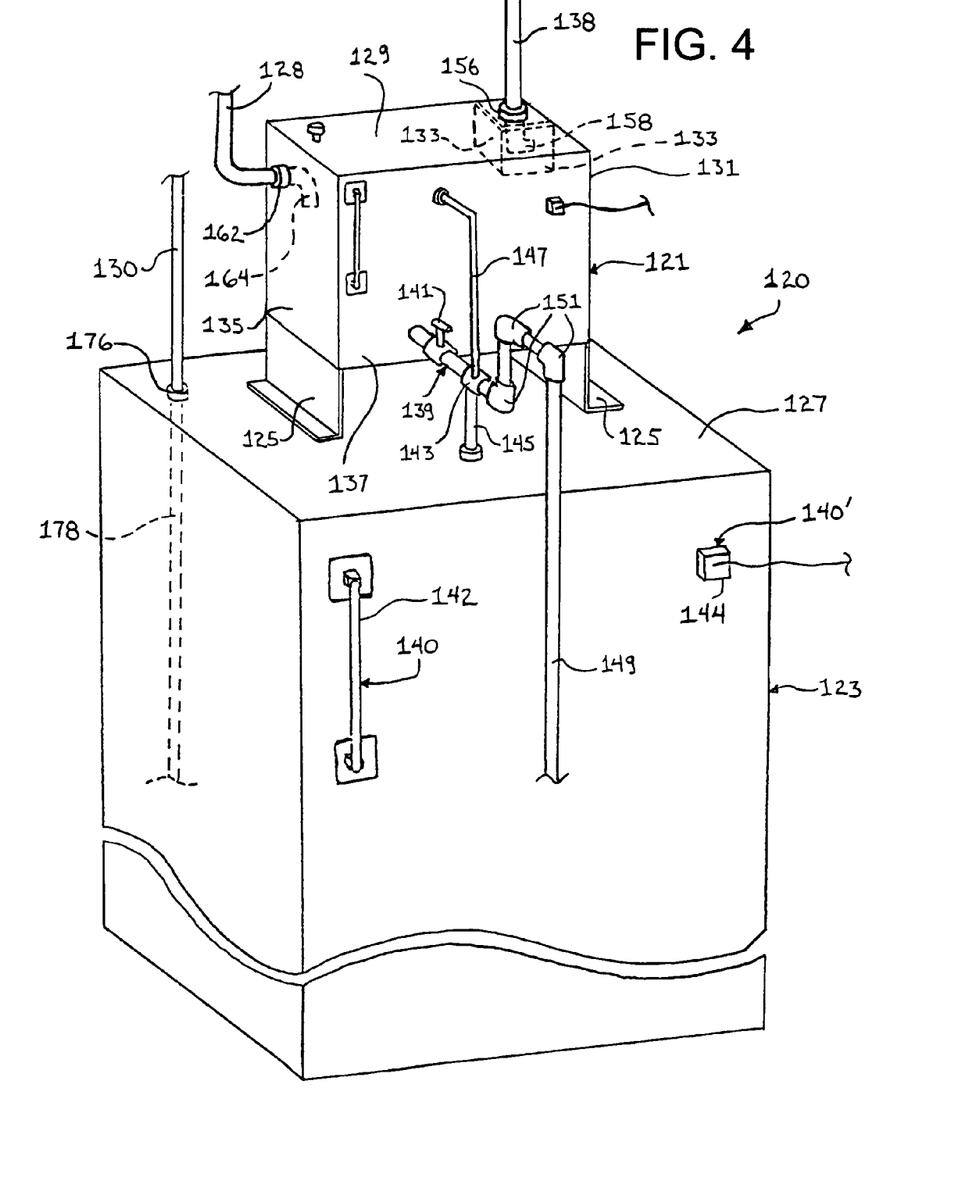
FIG. 4 is a perspective view of another dental waste containment system of the present invention.

Referring now to FIG. 4, an alternative dental waste containment system 120 is illustrated that may be generally fixedly mounted or installed within a facilities room or basement of a dental facility and used to collect, retain, and enable later removal of dental waste produced at the dental facility. The dental waste containment system 120 of FIG. 4 is of similar construction to dental waste containment system 20 above, with the similar components or elements of dental waste containment system 120 shown with similar reference numbers as used in FIGS. 1-3 with respect to dental waste containment system 120, but with 100 added to the reference numerals of FIGS. 1-3. It should be understood that, because of the similarity of the illustrated embodiments of the dental waste containment systems 20, 120, not all of the specific construction and alternatives of like referenced parts will be discussed in the following discussion of dental waste containment system 120.

Dental waste containment system 120 includes a first dental waste container or accumulator tank 121 mounted to a top 127 of a second dental waste container or storage tank 123 by supports 125 that space accumulator tank 121 from the top 127 of storage tank 123. A vacuum conduit or line 138 is attached to a top 129 of accumulator tank 121 at a vacuum connection 156 and a vacuum tube 158 extends into accumulator tank 121 at a ninety-degree angle directed to a side 131 of the accumulator tank 121. A vacuum pump (not shown) draws air or gas through accumulator tank 121 to produce a vacuum pressure therein for drawing dental waste through suction conduit or line 128. A filter (not shown) may also be included on vacuum conduit 138. Two baffles 133, each of which is constructed as an approximately two inch square metallic plate, are positioned in a perpendicular orientation relative to each other and to the sides of accumulator tank 121 about vacuum tube 158 to inhibit or impede dental waste drawn through suction conduit 128 from directly entering vacuum conduit 138.

Suction conduit or line 128 is attached to the side 135 of accumulator tank 121 opposite the side 131 at which vacuum tube 158 is directed and is attached to accumulator tank 121 at a suction connection 162. A suction tube or suction baffle 164 extends internally downward toward a bottom portion 137 of accumulator tank 121, with suction baffle 164 functioning, in part, to inhibit or impede dental waste drawn through suction conduit 128 from directly entering vacuum conduit 138. Although not show, suction conduit 128 extends into the various patient treatment rooms of the dental waste facility.

A first waste removal conduit or line 139 extends between the bottom portion 137 of accumulator tank 121 and the top 127 of storage tank 123 such that dental waste drawn into accumulator tank 121 may be transferred to storage tank 123. Waste removal conduit 139 includes both a valve 141 and a vacuum operated check valve 143, with a drain tube 145 extending from check valve 143 into storage tank 123. Check valve 143 includes a vacuum tube 147 attached to accumulator tank 121, with check valve 143 being maintained in a closed or fluid flow preventing position when accumulator tank 121 is subject to a vacuum pressure via the drawing of gas and/or air from accumulator tank 121 through vacuum conduit 138 by the vacuum pump. Conversely, when the vacuum pump is disconnected or a vacuum pressure is no longer supplied to accumulator tank 121, check valve 143 shifts to an open or fluid flow enabling position such that dental waste contained within accumulator tank 121 may flow through drain tube 145 and into storage tank 123, such as via gravity.

Thus, in operation, dental waste is drawn through suction conduit 128 into accumulator tank 121 and the dental waste remains contained within the accumulator tank 121 while the tank 121 is subject to vacuum pressure. Correspondingly, when the vacuum pressure within accumulator tank 121 is removed, dental waste contained within accumulator tank 121 may flow into storage tank 123.

The provision of an accumulator tank 121 and storage tank 123 in dental waste containment system 120 enables accumulator tank 121 to be constructed generally smaller than the dental waste container 24 of dental waste system 20 above, thus making it easier to create and maintain a vacuum within the accumulator tank 121. Further, storage tank 123 may be sized correspondingly larger than dental waste container 24 above to thereby decrease the frequency at which storage tank 123 must be emptied as compared to dental waste container 24.

Accumulator 121 tank may be constructed to have a volumetric capacity sufficient to retain approximately one days worth of dental waste or contaminated dental waste produced by a given dental facility based on the average or peak number of patients treated. For example, this may be approximately 2 to 3 gallons of dental waste, but of course may be more or less depending upon the size of the facility and the number of patients treated. Correspondingly, storage tank 123 may then be sized to accommodate multiple days worth of dental waste, with the contents of accumulator tank 121 being emptied into storage tank 123 on a daily basis. For example, storage tank 123 may be sized to contain between three to six months amount of dental waste, and thus have a volumetric capacity of between approximately 60 to 120 times greater than accumulator tank 121. Alternatively, the vacuum pressure applied to accumulator tank 121 may be removed two or more times a day, such as at a lunch break and in the evening, to allow the contents of accumulator tank 121 to drain into storage tank 123 more frequently. In the illustrated embodiment, accumulator tank 121 and storage tank 123 are constructed of a metallic material, such as aluminum or stainless steel. Alternative accumulator and/or storage tanks may, however, be constructed of a polymeric material.

FIG. 4 also discloses the inclusion of an overflow conduit or line 149 affixed to waste removal conduit 139. Overflow conduit 149 includes three ninety-degree bends or elbows 151 and is provided as a back-up dental waste flow route in the event storage container 123 becomes filled. Upon dental waste within storage container 123 reaching top 127, dental waste will flow up drain tube 145. Check valve 143 may be constructed as a one-way valve to prevent back flow from traveling toward accumulator tank 121. The overflow dental waste will then travel up and over the three elbows 151 and drain down overflow conduit 149, which may be fed to a secondary container or, alternatively, to a sewer line (not shown).

A second waste removal conduit or line or discharge conduit or line 130 extends into storage tank 123 to enable dental waste contained therein to be removed by suctioning or pumping the dental waste out, as noted generally above and described in more detail below. Discharge conduit 130 is connected to a discharge tube 178 extending into storage tank 123 at discharge connection 176. In the illustrated embodiment, discharge conduit 130 is formed of 1 inch diameter PVC tubing, but may alternatively be formed of copper tubing, galvanized pipe, or the like.

FIG. 4 also illustrates the inclusion of indicators 140, 141' constructed as visual gauges 142 and electronic gauges 144 on both the storage tank 123 and accumulator tank 121, where electronic gauges 144 may comprise audible and/or light indicating gauges. Although both storage tank 123 and accumulator tank 121 are shown as including both visual gauges 42 and electronic gauges 144, it should be understood that storage tank 123 and accumulator tank 121 may alternatively be constructed to include only one of such gauge types, or one or both of such gauges may be included on only one of the storage and accumulator tanks, or the storage and accumulator tanks may be constructed without such gauges.

Figure 5:
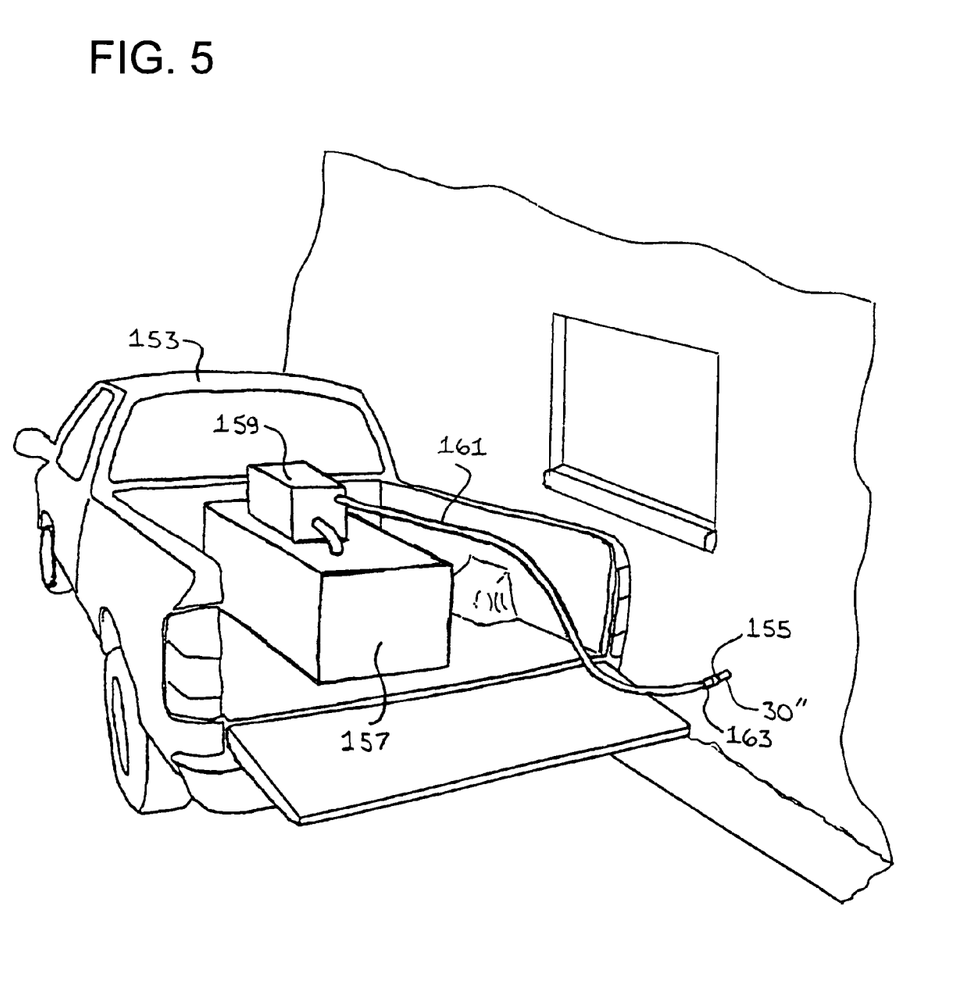
FIG. 5 is a perspective view of a service vehicle removing dental waste from a dental waste container from an exterior location of a dental services facility.

Referring now to FIG. 5, a service vehicle or truck 153 is illustrated removing dental waste from dental waste facility 20. As previously noted, a waste removal conduit 30", which may be part of dental waste containment system 20 or 120, extends through and out of external wall 32 of dental facility 20. Waste removal conduit 30" includes a valve or connector, which in the illustrated embodiment is a quick-connector type fitting 155. Truck 153 includes a transport tank or vessel 157 and a pump 159, which may be constructed as an air compressor type pump or electric pump. A hose 161 having a mating fitting 163 adapted to connect to the fitting 155 of waste removal conduit 30" extends from pump 159 such that pump 159 may transfer dental waste from a dental waste container to transport tank 157.

Truck 153 may then be used to transport the dental waste to a treatment facility, such as a treatment facility licensed or authorized to handle hazardous materials. Dental waste containing mercury may be treated through a reclamation process whereby the mercury is removed from the dental waste. The remaining mercury free dental waste may then be further treated or may, in some cases, be properly released to sewer lines for treatment at municipal waste water treatment plants. Alternatively, dental waste containing mercury may be treated using a centrifuge or autoclave process, or may be handled as solid waste or processed via an incineration process in accordance with local, state, and federal regulations.

Figure 6:
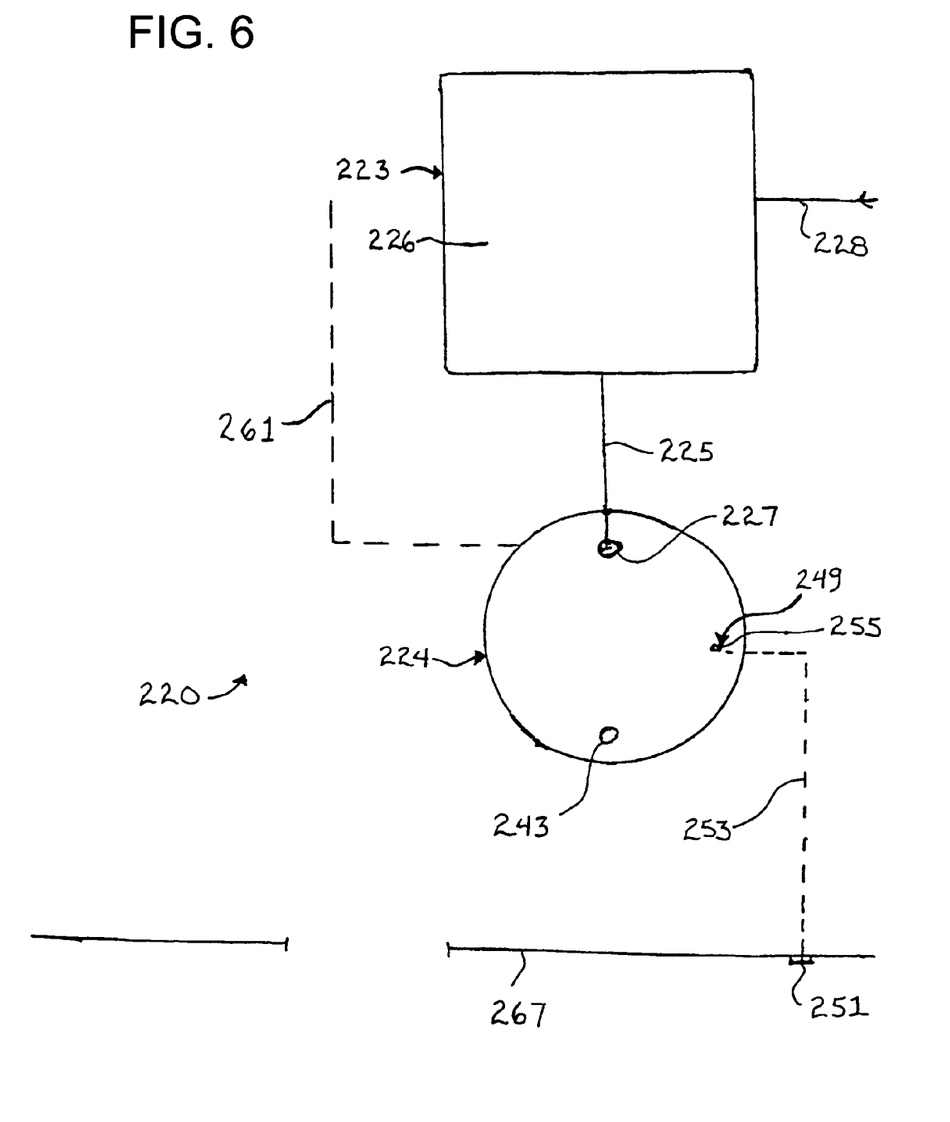
FIG. 6 is a partial schematic top plan view of another dental waste system of the present invention within a dental facility.
Figure 7:
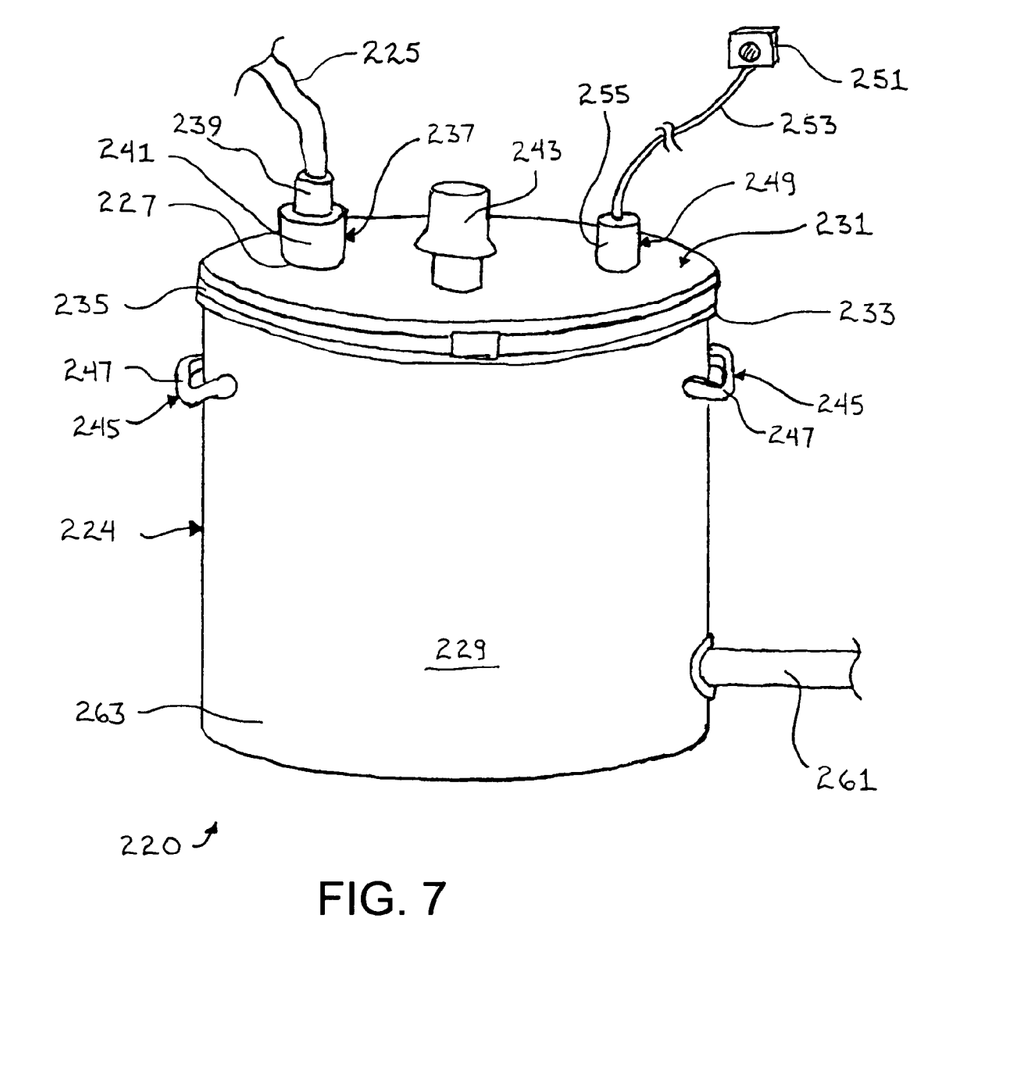
FIG. 7 is a perspective view of the dental waste containment system of FIG. 6.

Referring now to FIGS. 6 and 7, another dental waste containment system 220 is illustrated that incorporates or utilizes an existing suction device or dental evacuation device 223 located within a dental facility. The suction device 223 includes a suction or vacuum pump 226 connected to each of the individual rooms of the dental facility through a suction line 228, with the suction line 228 within each room being fitted, for example, with a conventional saliva ejector. When necessary, a dentist or dental hygienist may insert the saliva ejector into the mouth of a dental patient and activate the equipment by a foot pedal, or thumb switch, or the like (not shown), such that dental waste within the patient's mouth is removed and drawn into suction line 228. Optionally, a jet or stream of water may be squirted into the patient's mouth to aid in the rinsing and suctioning of the waste matter from the patient's mouth. Still further, a conventional dental sink (not shown) into which patients may spit dental waste may be in fluid communication with suction line.

As shown in FIG. 6, suction device 223 is in fluid communication with dental waste container 224 through fluid inlet line 225 whereby suction device 223 is able to transfer all of the dental waste removed from the mouths of patients serviced at the dental service facility to the dental waste container 225. Therefore, dental waste containing a contaminant, such as suspended mercury, is prevented from entering a sewer line (not shown) or from entering the ground water.

Inlet line 225 transfers dental waste drawn from the mouths of patients to dental waste container 224, the dental waste being transferred through inlet opening 227 on dental waste container 224. The illustrated embodiment of FIG. 7 discloses that dental waste container 224 is constructed as a generally cylindrical drum, tank, or vessel. Dental waste container 224 may be constructed to have a volumetric capacity of between approximately five and fifty-five gallons, with the volume of the dental waste container 224 utilized being selected based upon the size of the dental practice or dental service facility.

Although dental waste container 224 is disclosed as being generally cylindrical, it should be understood that dental waste container 224 may be alternatively constructed to have a non-cylindrical form, such as cubic or spherical, and still function as intended. Dental waste container 224 may be constructed of a polymeric material or a metallic material that is either corrosion resistant or treated with a coating to provide corrosion resistance.

Dental waste container 224 includes a body 229 and a top member 231, with top member 231 being constructed as a sealed, removable lid 233 in the embodiment illustrated in FIG. 7. Lid 233 is secured to container 224 by a securing member or locking ring 235 such that lid 233 and securing member 235 prevent the contents of dental waste container 224 from leaking out. Securing member 235 may be constructed to receive a lock or security device (not shown) that enables only authorized personnel to access dental waste container 224 and thereby prevent unwanted opening of dental waste container 224.

It should be understood, however, that dental waste container 224 need not include securing member 235 and may still function as intended. For example, lid 233 could be threaded or snapped into engagement with body 229. Alternatively, dental waste container 224 may be constructed to not include a removable lid 233. For example, dental waste container 224 could be constructed of a polymeric material and molded to form an integrated top member, with an inlet hole being provided that is adapted to receive inlet line 225. Similarly, a lid of metallic material may be provided that is fixedly welded or crimped on a metallic dental waste container.

In the illustrated embodiment of FIG. 7, inlet line 225 is a flexible hose and is affixed to dental waste container 224 by a connector 237. In the preferred embodiment shown, connector 237 is a quick-disconnect type connector of known construction having an insertion member 239 secured to flexible inlet line 225 and a receiving member 241 on lid 233 adapted to receive the insertion member 239. It should be understood that alternative connector types or methods may be used, such as threaded connectors or the like, without affecting the intended function.

FIG. 7 also discloses that dental waste container 224 includes a filter 243 secured to top member 231. Filter 243 enables the internal pressure of the air located above the dental waste contained within dental waste container 224 to balance with ambient conditions outside of the dental waste container 224 while preventing dental waste from escaping dental waste container 224. In a preferred embodiment, filter 243 is a HEPA filter that substantially prevents or inhibits odors from escaping the dental waste container 224. Alternatively, filter 243 may be constructed as a charcoal filter, or the like, and still function as intended.

The illustrated embodiment of FIG. 7 also discloses that dental waste container 224 includes transport members 245 on body 229, where transport members 245 are shown as being handles 247 on opposite sides of dental waste container 224. Handles 247 enable efficient transportation of dental waste container 224 such that the dental waste container 224 may be removed from the dental services facility as described below. Although transport members 245 are disclosed as handles 247, it should be understood that alternative types and styles of transport members 245 may be employed that would also enable dental waste container 224 to be easily transported. For example, transport members could be formed as tabs or grooves that enable a two-wheeled dolly, or the like, to engage the dental waste container. Transport members may also be formed as recessed handholds within the body, or the like. Still further, transport members could be constructed as wheels affixed to a dental waste container, or the like.

As shown in FIG. 7, dental waste container 224 also includes an indicator, which in the embodiment illustrated is a gauge 249 that is adapted to provide an indication of the quantity of dental waste contained within dental waste container 224. Gauge 249 is thus able to alert dental service facility personnel of the need for dental waste container 224 to be emptied or replaced in the manners described below. In the illustrated embodiment, gauge 249 includes a warning light 251 that is adapted to receive a signal through a line 253 from a base unit 255 installed on dental waste container 224. As understood from FIG. 6, dental waste container 224 may be positioned at a location 257 removed from where personnel of the dental services facility would provide service to patients. Therefore, warning light 251 may be installed in a service providing location 259 with line 253 extending between warning light 251 and base unit 255.

Although gauge 249 is disclosed above as including a warning light 251, it should be appreciated that gauge 249 may be alternatively constructed and still function as intended to provide an indication of the quantity of dental waste contained within dental waste container 224. For example, a warning light could be mounted directly to a dental waste container or a base unit, or warning light could include known wireless communication technology such that line would not be needed. Alternatively, warning light 251 may be replaced with an audio alert (not shown) adapted to emit an audible signal upon dental waste within dental waste container 224 reaching a predetermined level. Furthermore, dental waste container 224 could include a gauge constructed as a transparent or translucent member enabling visual observation of the level of dental waste within dental waste container 224.

FIG. 7 illustrates that dental waste container 224 may be optionally constructed to include a discharge outlet 261 adapted to enable dental waste to be removed from dental waste container 224. Discharge outlet 261 would preferably be located proximate the end 263 of dental waste container 224 resting on a support surface such that dental waste would be able to flow out of dental waste container 224 via gravitational forces. However, a pumping mechanism could also be utilized to remove the dental waste. Discharge outlet 261 may also include a valve (not shown) whereby a removal hose could be connected to discharge outlet 261 prior to opening the valve such that leakage of dental waste would be limited or substantially precluded.

In similar manner to dental waste containment systems 20, 120, for example, discharge outlet 261 may extend through an exterior wall of the dental services facility. In such a configuration, dental waste may be removed from dental waste container 224 without moving dental waste container 224 or without the need for bringing additional equipment into the dental services facility. A lockable cap (not shown) may be provided on discharge outlet 261 to prevent unwanted opening. Discharge outlet 261 may alternatively extend through an interior wall 267 of dental services facility. This latter configuration being beneficial, for example, when dental waste container 224 is located in a generally inaccessible location.

When the level of dental waste within a dental waste container (224) reaches a predetermined level it is necessary to transport the dental waste to a facility for treatment. To transport the dental waste from the dental services facility, an authorized transporter may enter the dental services facility, disconnect the inlet line (225) from the dental waste container (224), plug the inlet opening 227, and reconnect the inlet line (225) to an empty dental waste container (224). Alternatively, as noted above, the dental waste may be drained or pumped from the dental waste container (224). Still further, the dental waste may be emptied from the container (224) into a transport vessel (not shown) and the original dental waste container (224) re-connected to the inlet line (225). Also, if the dental waste container (224) includes a gauge 249 and/or a filter (243), these devices may be removed prior to transport with their respective mounting openings being plugged during transport. It should be appreciated that removal of the dental waste could be achieved, for example, by establishing a program whereby upon notification or upon an established schedule an authorized transporter would go to the dental services facility for such purpose.

The present invention provides an effective dental waste containment system and method for preventing contaminated dental waste from entering a sewer line and/or ground water. The dental waste captured in the dental waste container may be easily pumped out of the dental waste container from a remote location, such as through an exterior wall of the dental facility to a transport tank on a service vehicle. The dental waste may then be readily delivered to a treatment facility that is able to effectively remove or treat contaminants such as mercury. The providing of indicators or gauges on the dental waste containers provides an effective method of notifying the dental services facility personnel that the dental waste container has been filled with a predetermined level of dental waste and needs to be emptied or replaced. Further, a dental waste containment system constructed to include two dental waste containers, one of which functions as an accumulator tank and the other as a storage tank, provides an effective construction for collecting, for example, daily waste and retaining longer term waste.

The above is a description of the preferred embodiments. One skilled in the art will recognize that changes and modifications may be made without departing from the spirit of the disclosed invention, the scope of which is to be determined by the claims which follow and the breadth of interpretation that the law allows.

The embodiment of the invention in which we claim an exclusive property right or privilege are as follows:

1. A dental waste system for containing and removing substantially all contaminated dental waste including contaminates in suspension produced at a dental facility without discharge to a sewer, said dental waste system comprising:
   a first dental waste container generally fixedly installed within a dental facility, said first dental waste container being adapted to receive contaminated dental waste;
   a second dental waste container generally fixedly installed within the dental facility, said second dental waste container having a volumetric capacity greater than said first dental waste container;
   a vacuum conduit connected to said first dental waste container;
   a vacuum pump connected to said vacuum conduit to selectively generate a vacuum pressure within said first dental waste container;
   a suction conduit in fluid communication with said first dental waste container and operable in response to a vacuum pressure generated by said vacuum pump to transfer dental waste containing a contaminant from the mouth of a dental patient to said first dental waste container whereby substantially all contaminated dental waste is contained within said first dental waste container including contaminates in suspension;

a waste removal conduit, said waste removal conduit being in fluid communication with said first dental waste container and said second dental waste container and adapted to transfer substantially all dental waste from said first dental waste container into said second dental waste container, said waste removal conduit including a check valve and a vacuum tube being connected to said check valve with said vacuum pump selectively generating a vacuum pressure within said vacuum tube, said check valve being responsive to deactivation of said vacuum pump to enable dental waste to flow from said first dental waste container to said second dental waste container when said vacuum pump ceases generating a vacuum pressure within said vacuum tube; and a discharge conduit, said discharge conduit being fluidly connected to said second dental waste container and enabling substantially all dental waste including contaminates in suspension to be removed from the dental facility without any fluids or dental waste being discharged to a sewer.

2. The dental waste system of claim 1, further including a transport vessel and a transport pump, said transport vessel being selectively fluidly connected to said second dental waste container and wherein the dental waste is selectively pumped out of said second dental waste container through said discharge conduit into said transport vessel via said transport pump whereby the dental waste may be transported to a treatment facility.

3. The dental waste system of claim 1, wherein said discharge conduit extends out of an exterior wall of said dental facility to an exterior location of said dental facility.

4. The dental waste system of claim 1, wherein said first dental waste container is positioned generally vertically higher than said second dental waste container such that the dental waste is able to drain via gravity from said first dental waste container to said second dental waste container upon deactivation of said vacuum pump.

5. The dental waste system of claim 1 including an indicator on said second dental waste container, said indicator being adapted to indicate the level of dental waste contained within said second dental waste container.

6. The dental waste system of claim 5, wherein said indicator is at least one chosen from a visual gauge, a light indicating gauge, and an audible indicating gauge.

7. The dental waste system of claim 1, wherein said first dental waste container has a volumetric capacity greater than the approximate daily volumetric amount of dental waste produced at said dental facility, and wherein said second dental waste container has a volumetric capacity greater than said first dental waste container to hold a plurality of daily volumetric dental waste amounts.

8. The dental waste system of claim 1, wherein said vacuum tube extends from said check valve to said first dental waste container such that said vacuum pump selectively generates a vacuum pressure within said vacuum tube simultaneously with a vacuum pressure within said first dental waste container.

9. A dental waste system for containing and removing substantially all contaminated dental waste including contaminates in suspension produced at a dental facility without discharge to a sewer, said dental waste system comprising:

a first dental waste container generally fixedly installed within a dental facility, said dental waste container being adapted to receive contaminated dental waste;

a second dental waste container generally fixedly installed within the dental facility, said second dental waste container receiving contaminated dental waste from said first dental waste container;

a vacuum conduit and a vacuum pump, said vacuum conduit connected to said first dental waste container with said vacuum pump connected to said vacuum conduit and adapted to selectively generate a vacuum pressure within said vacuum conduit;

a suction conduit, said suction conduit being fluidly connected to said first dental waste container and operable in response to a vacuum pressure generated by said vacuum pump to transfer dental waste to said first dental waste container whereby contaminated dental waste is initially contained within said first dental waste container including contaminates in suspension;

a waste removal conduit, said waste removal conduit being in fluid communication with said first dental waste container and said second dental waste container and adapted to selectively transfer dental waste from said first dental waste container into said second dental waste container, said second dental waste container having a volumetric capacity greater than a plurality of the volumetric capacity of said first dental waste container;

a check valve on said waste removal conduit and a vacuum tube connected to said check valve with said vacuum pump selectively generating a vacuum pressure within said vacuum tube, said check valve being responsive to deactivation of said vacuum pump to enable dental waste to flow from said first dental waste container to said second dental waste container when said vacuum pump ceases generating a vacuum pressure within said vacuum tube;

a discharge conduit, said discharge conduit being fluidly connected to said second dental waste container; and a transport vessel and a transport pump, said transport vessel being selectively fluidly connected to said discharge conduit and wherein dental waste is selectively pumped out of said second dental waste container through said discharge conduit into said transport vessel via said transport pump whereby dental waste including contaminates in suspension is removed from the dental facility without being discharged to a sewer thereby enabling the dental waste to be transported to a treatment facility.

10. The dental waste system of claim 9, further including a transport vehicle, said transport vessel and said transport pump being installed on said transport vehicle.

11. The dental waste system of claim 10, wherein said discharge conduit extends out of an exterior wall of said dental facility to an exterior location of said dental facility.

12. The dental waste system of claim 9, wherein said first dental waste container is positioned generally vertically higher than said second dental waste container such that the dental waste is able to drain via gravity from said first dental waste container through said waste removal conduit to said second dental waste container.

13. The dental waste system of claim 12, wherein said first dental waste container has a volumetric capacity greater than the approximate daily volumetric amount of dental waste produced at said dental facility, and wherein said second dental waste container has a volumetric capacity greater than said first dental waste container to hold a plurality of daily volumetric dental waste amounts.

14. The dental waste system of claim 9, wherein said vacuum tube extends from said check valve to said first dental waste container such that said vacuum pump selectively generates a vacuum pressure within said vacuum tube simultaneously with a vacuum pressure within said first dental waste container.

* * * * *